United States Patent [19]

Brooks

[11] Patent Number: 4,627,428

[45] Date of Patent: Dec. 9, 1986

[54] CHILD RESTRAINT DEVICE WITH REMOVABLE SEMI-RIGID SUPPORT

[76] Inventor: David A. Brooks, 165 LaRose Avenue, Suite 106, Weston, Ontario, Canada, M9P 3S9

[21] Appl. No.: 641,877

[22] Filed: Aug. 17, 1984

Related U.S. Application Data

[63] Continuation-in-part of Ser. No. 619,018, Jun. 11, 1984, abandoned.

[51] Int. Cl.⁴ ............................................. A61F 13/00
[52] U.S. Cl. ..................................... 128/135; 5/82 R
[58] Field of Search .................... 128/134, 135; 5/424, 5/82 R, 494, 413, 82

[56] References Cited

U.S. PATENT DOCUMENTS

| | | | |
|---|---|---|---|
| 2,279,694 | 4/1942 | Martinson | 5/82 |
| 2,309,464 | 6/1943 | Lucci et al. | 5/82 |
| 2,324,665 | 7/1943 | Ayres | 5/413 |
| 2,456,898 | 12/1948 | Strandhagen | 128/134 |
| 2,563,501 | 8/1951 | Sperling | 128/134 |
| 2,643,390 | 6/1953 | Ramsland | 2/310 |
| 2,643,398 | 6/1953 | Routman | 5/334 |
| 2,675,564 | 4/1954 | Hughes | 5/82 |
| 2,763,264 | 9/1956 | McInnerny | 128/133 |
| 3,003,164 | 10/1961 | Cavelage | 5/343 |
| 3,110,912 | 11/1963 | Propst | 5/82 |
| 3,204,256 | 9/1965 | Stollenwerk | 5/82 |
| 3,521,309 | 7/1970 | Evans | 5/336 |
| 3,707,734 | 1/1973 | Matthews | 5/82 |
| 3,831,206 | 8/1974 | Geary | 5/413 |
| 3,840,221 | 10/1974 | Hogan | 5/82 |
| 3,878,844 | 4/1975 | Tobias | 128/134 |
| 3,889,668 | 6/1975 | Ochs et al. | 128/134 |
| 4,006,500 | 2/1977 | Bonifay | 5/82 R |
| 4,064,574 | 12/1977 | Schnitzler | 5/82 R |
| 4,074,375 | 2/1978 | Kella | 5/336 |
| 4,115,884 | 9/1978 | Keogh | 5/82 R |
| 4,124,908 | 11/1978 | Burns et al. | 5/82 R |
| 4,127,120 | 11/1978 | Applegate | 128/134 |
| 4,169,428 | 10/1979 | Waugh | 119/1 |
| 4,186,453 | 2/1980 | Burns et al. | 5/82 R |
| 4,241,466 | 12/1980 | Mendyk | 5/497 |
| 4,283,068 | 8/1981 | Keyser | 5/82 B |
| 4,347,635 | 9/1982 | Eisenhauer | 5/82 R |
| 4,369,982 | 1/1983 | Hein et al. | 5/82 R |
| 4,413,368 | 11/1983 | Schuetze | 5/494 |

*Primary Examiner*—F. Barry Shay
*Attorney, Agent, or Firm*—Weingarten, Schurgin, Gagnebin & Hayes

[57] ABSTRACT

There is described a child safety restraint for restraining a child in a substantially flat position relative to a medical transporting device. The apparatus includes a child support device that includes a semi-rigid base and a cover attachable to the base so as to secure the child between the base and the cover. The base includes two layers of material and a semi-rigid support insertable between the layers of material. The lower layer of material has apertures through which fastening members of the semi-rigid support extend. The apparatus further includes a restraining harness for interconnecting the fastening members of the child support with the transporting device such that movement of the child support relative to the transporting device is restrained.

12 Claims, 12 Drawing Figures

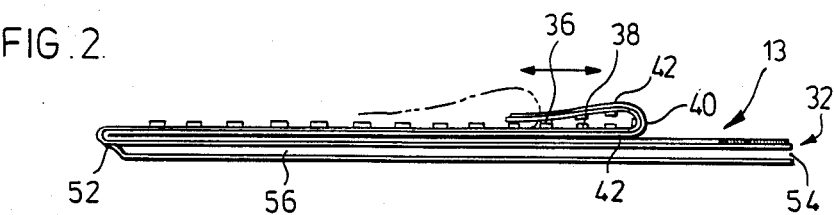
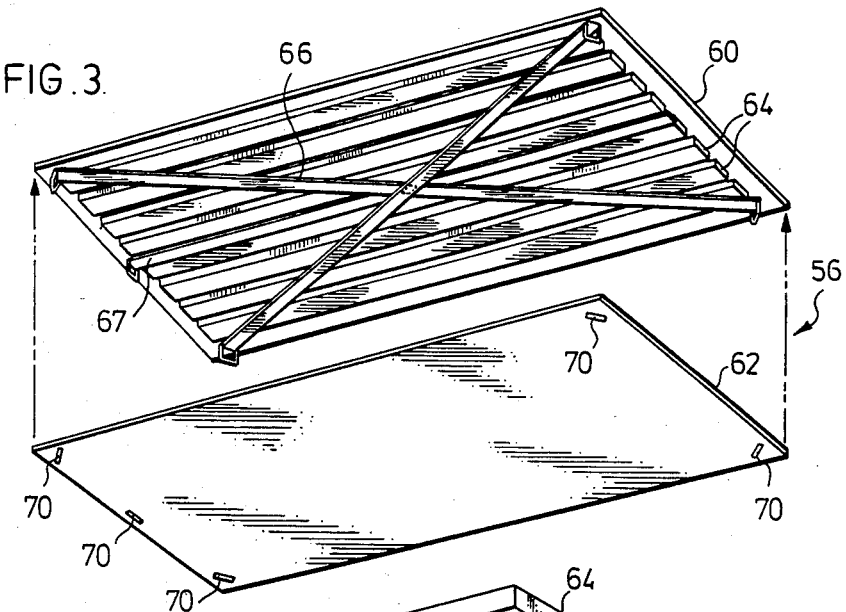
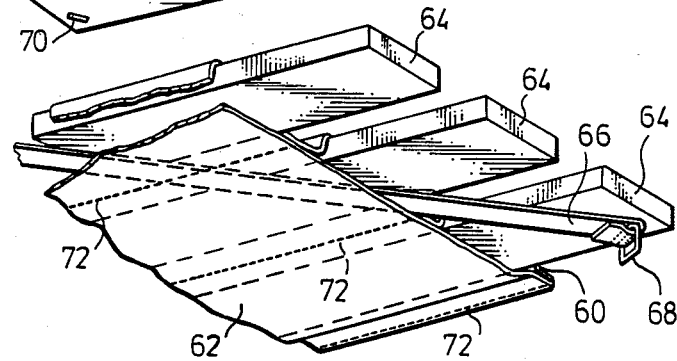
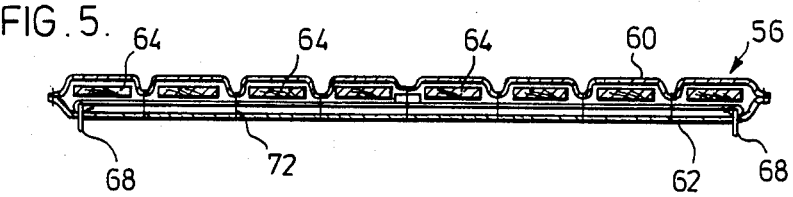

CHILD RESTRAINT DEVICE WITH REMOVABLE SEMI-RIGID SUPPORT

This application is a Continuation-in-Part of application Ser. No. 619,018 filed June 11, 1984, now abandoned.

The present invention relates to a child safety restraining apparatus for use with medical transporting equipment. In particular, it relates to a safety apparatus for transporting children in ambulances and/or on stretchers.

Government regulatory bodies in varies jurisdictions are becoming increasing concerned with the safety of children travelling in motorized vehicles. Many of these regulatory bodies have approved legislation requiring minimum safety standards for children who travel in an automobile. These safety standards apply, in particular, to children having body weights below about 20 kilograms. Those regulatory bodies that have not as yet passed legislation in this regard, may well be in the process of reviewing minimum safety standards for children travelling in automobiles and the like.

As the result of the legislation enacted by various governments, there has been in recent years an abundance of new child safety seats which safely secure a child within an automobile or like vehicle.

At present, there is not believed to be any existing safety device for restraining movement of a child in a medical transporting device such as an ambulance or on a stretcher which may be secured in an ambulance. Stretchers used in ambulances are normally provided with two restraining straps. These straps are positionable over the thorax and shins of an adult. The straps effectively restrain the position of the adult in an ambulance to minimize risk of injury to the adult. As can be appreciated, the location of these straps is not acceptable for restraining children who are under about 4'8" in height. As a result, all children below this height, such as infants, for example, must be held by an ambulance attendant, relative, or any other individual during the transportation of the child to a hospital. This does not minimize risk to the child during transportation in the event of sudden changes in ambulance motion or in the event of an ambulance accident. As can be appreciated, sudden changes of ambulance motion may result in further complications to the child's health such as, for example, an aggravation of injuries previously sustained and/or the improper functioning of health care equipment used to stabilize the child's condition. Also, new injuries to the child or others travelling in the vehicle may result from violent displacement of the child in the ambulance. These injuries may be serious and result in death.

Accordingly, it is one object of the present invention to provide a child safety restraining apparatus that restrains the apparatus and child to a medical transportation device.

It is another object of the present invention to provide a child safety restraining apparatus that restrains a child support in which the child is protectively secured.

It is another object of the present invention to provide a child safety restraining apparatus for use with medical transporting devices that allows access to the child for the purpose of administrating health care to the child during transportation.

Another object of the present invention is to provide a child safety restraining apparatus for use with medical transporting devices that is adjustable to accommodate children of varying sizes including infants weighing about onehalf a kilogram.

It is still another object of the present invention to provide a child safety restraining apparatus for use with medical transporting devices that may be readily sanitized.

In accordance with one aspect of the present invention there is provided a child safety restraining apparatus for restraining a child in a substantially flat position relative to a medical transportating device. The restraining apparatus comprises child support means including a semirigid or rigid base comprising upper and lower layers of material joined along or adjacent side edges thereof to provide a pocket between the layers of material which is open at one end thereof. The lower layer of material has a plurality of apertures located at predetermined locations therein. The base includes a semi-rigid or rigid support member insertable into the pocket through the open end. The support member includes fastening members secured to the lower surface thereof at predetermined positions which correspond to the locations of the apertures in the lower layer of material such that each of the fastening members extends through a corresponding aperture when the support member is inserted in the pocket. The child support means further includes a cover attachable to the upper layer of the material to protectively secure the child between the upper layer of material of the base and the cover. The apparatus further includes restraining means for interconnecting the child support means with the transporting device whereby movement of the child support means relative to the transporting device is restrained.

By restraining movement of the child support means in the manner described above, the child support means is held in position should the transporting device such as an ambulance, be involved in an impact or sudden change in its movement. The child is protectively secured in the child support means such that any movement of the child relative to the child support means is minimized. Because adverse forces act primarily upon the apparatus, the risk of injury to the child is reduced.

It should be understood that for smaller children such as infants or children weighing less than 20 kilograms, the child's center of gravity is closer to its head than the center of gravity for an adult. In the event of a sudden impact the child, who is very flexible, can flex about its center of gravity causing spinal or internal trauma, such as whiplash or splenic rupture for example. By using a semirigid or rigid base, the base provides rigidity to the child support means that compensates for the child's flexibility. This minimizes the risk of injury.

The child is restrained in a substantially flat position such that any movement of the child relative to the child support means during adverse vehicle movement results in the child shifting laterally, However, the attachment of the cover to the base prevents the child from being forced out of the child support means. It should be understood that the substantially flat position is a supine or a phone position in most instances.

It should also be understood that by reference to a child safety restraining device, the term "safety" is used in the context that the device is designed with materials which will allow it to be of a standard above or equal to any minimum safety standards set out by government regulatory bodies.

The restraining apparatus may comprise a harness that is fastened to the child support means and the transporting device. The harness may surround the child support means so as to also restrain movement of the child. It should also be understood that the harness may be used by itself for older children and that the child support means, which is a bag-like object, is for use with children whose weight is less than about 30 kilograms. The harness preferably includes two shoulder straps, two leg straps and a perineal strap. The straps are adjustable in length to comfortably pass over the child, are secured to one another below the child support means, and are securable by a suitable buckle or the like above the child support means. Additionally, the straps may include an attachment strap which has a fastening member at its end. The attachment strap and fastening member are used to secure the harness to the medical transporting device.

It is further envisaged that the cover may be foldable so as to adjust in size. The cover means preferably comprises a blanket-like material having a series of male and female fasteners spaced along the side edges of the upwardly facing surface of the cover means such that as the cover is folded, the male and female fasteners are snapped together. This feature adjusts the size of the cover so that it does not completely overlie the child but allows the child's head to protrude above the cover.

It is envisaged that the cover may at least be partially detachably attached to the base means so as to permit access to the child at various locations along the edge of the child support means for administration of health care equipment.

In the preferred construction, strips of adhesive material such as "velcro" (a trademark), may extend along the inner surfaces of and adjacent the periphery of the cover and the base. The adhesive material of the cover engages the adhesive material of the base to provide the detachable attachment.

The child support means preferably includes two discrete members so as to facilitate its cleaning should it become soiled. The base comprises upper and lower layers of material joined along or adjacent edges thereof to provide a pocket between the layers which is open at one end. In particular the bottom and two side edges of the two layers of material are joined and the top edges of the two layers are not joined. It should be understood that reference to "layer of material" may include within its scope, but is not necessarily limited to a blanket like member comprising two sheets sewn together and having a thermal or protective filler between the sheets. The base may further include a flap which covers the open end and is securable over the opening by the fastening members further extending through apertures in the flap. The base further includes a semi-rigid support member which is insertable into this pocket.

The semi-rigid support member includes a series of elongate reinforcing members equidistantly spaced apart from each other and secured between two layers of material by sewing or the like so as to make the support rigid in one direction and flexible in a second direction orthogonal to the first direction. This allows the semi-rigid support member to curl about the child and provides further support for small infants. The reinforcing members extend in a direction parallel to the direction that the backbone of the infant is expected to extend to make the semi-rigid support rigid in this direction. This one direction may be referred to as the longitudinal direction. This prevents the child from flexing along this part of its body in the event of sudden disturbances in the movement of the medical transportation. When the slats or reinforcing members are spaced apart from each other the semi-rigid support member may be partially wrapped about the child should this type of support be required by the child.

The semi-rigid support means preferably includes support webbing extending from corners of the support and one intermediate point which cross over each other. The ends of the support webbing adjacent the corners and the edge of the support are provided with fastening members. The lower layer of the base is provided with apertures through which the fastening members of the semi-rigid support extend for connection with the harness. In this manner, the base of the child support means is restrained by the harness. The harness passing around the child support means acts to restrain the child.

In accordance with one aspect of the present invention there is provided a child safety support apparatus comprising semi-rigid or rigid base and cover attachable to the base to secure a child in a substantially flat position between the base means and the cover means.

For a better understanding of the nature and objects of the present invention, reference may be had by way of example to the accompanying diagrammatic drawings in which:

FIG. 2 is a side sectional view of the child support bag of the apparatus showing the adjustment of the cover;

FIG. 3 is an exploded perspective view of the semi-rigid support of the apparatus;

FIG. 4 is a partially exploded view of the construction of the semi-rigid support;

FIG. 5 is a side sectional view of the semi-rigid support;

Figure 1:
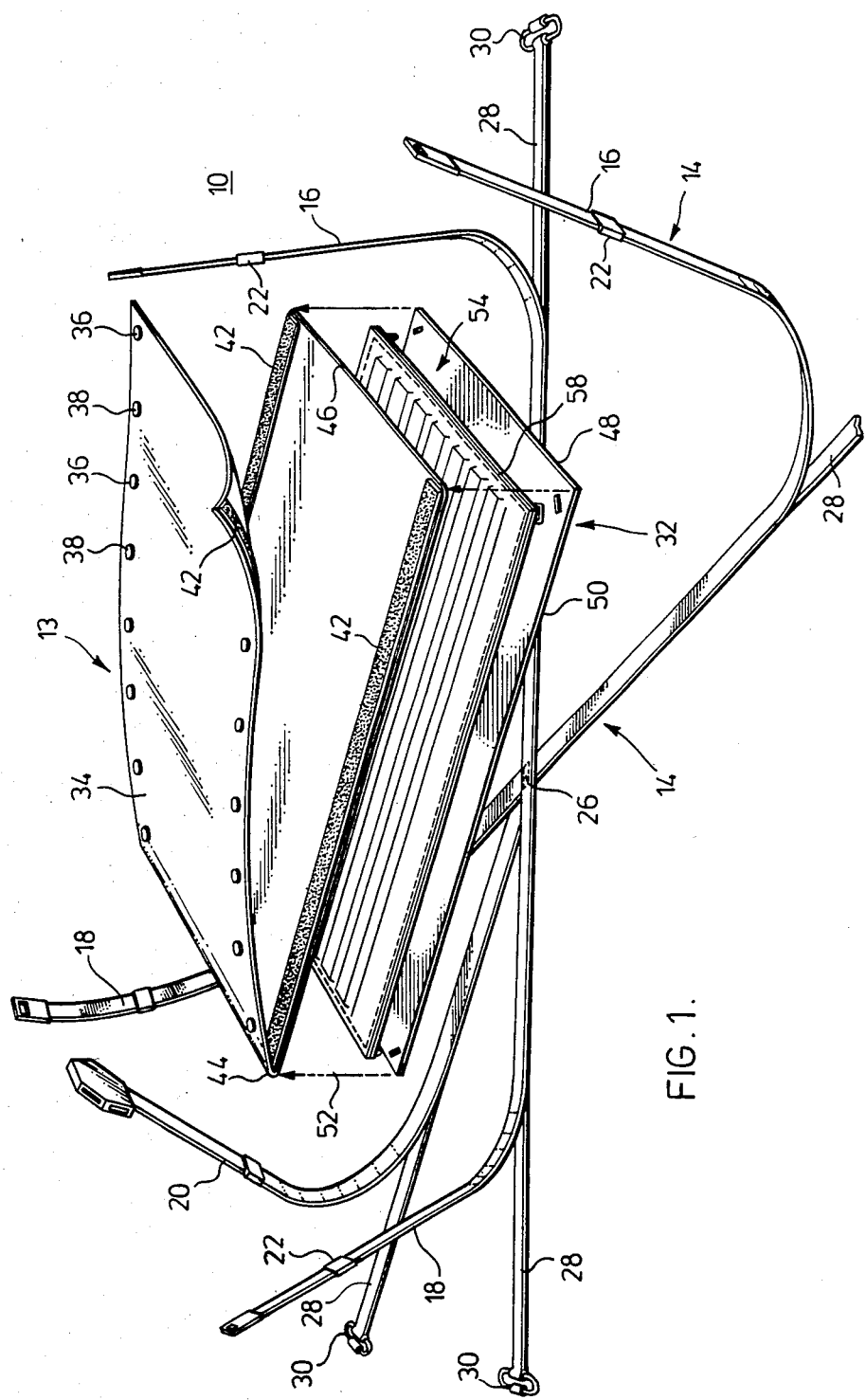
FIG. 1 is a partially exploded perspective view of the child safety restraining apparatus of the present invention.

Referring to the Figures, there is shown a child safety restraining apparatus 10 for restraining a child 11 in a supine position relative to a medical transporting device such as ambulance 12. The apparatus 10 includes a child support means or bag-like support 13 and a restraining means in the form of a harness 14.

The harness 14 comprises shoulder straps 16, leg straps 18 and a perineal strap 20. Each of these straps is adjustable by means of brackets or buckles 22 (FIGS. 6 and 8) and are secured at a central buckle 24. The underside of the harness of each of these straps is sewn together at 26 (FIG. 1). As shown in the drawings, each of these support straps is provided with an adjustable attachment strap 28 which is provided with a fastening member 30 which may be secured to a rigid or fixed point on or in ambulance 12. As shown in the drawing, the harness 14 passes below and above the child support 13.

Figure 6:
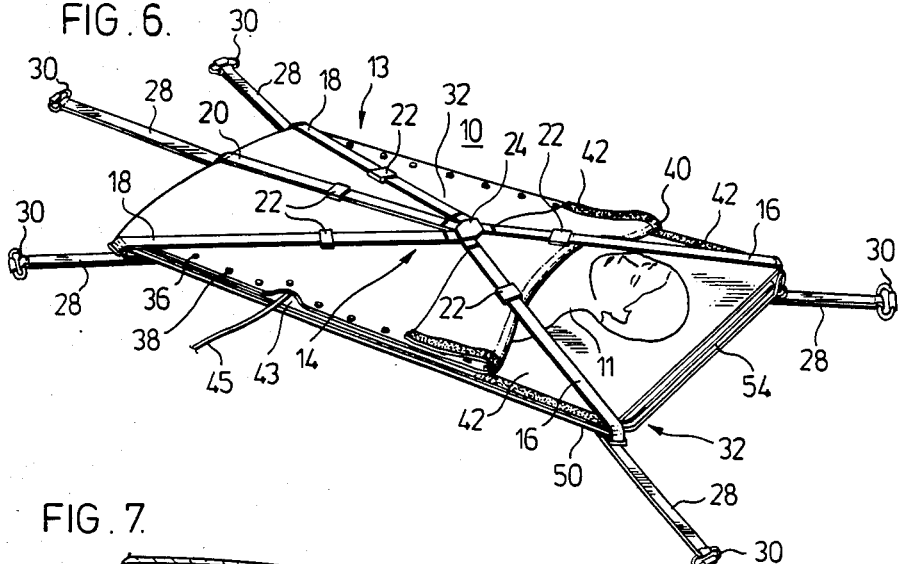
FIG. 6 is a perspective view of the apparatus of the present invention restraining a child.

The child support 13 is designed to restrain the child in a supine position on a medical transporting device such as a stretcher or any other flat or relatively flat surface. The child support 13 includes a semi-rigid base 32 and a cover 34. The cover 34 is provided with a series of male and female domes 36, 38 which extend along opposing ends of the cover as shown in the drawings. The cover may be folded at 40 (FIGS. 6 and 8) to adjust the size of the cover so that it does not lie over the child and the child is securely located within the child support 13. On the underside of the cover 34 there is provided an adhesive material in the form of Velcro strips 42. Velcro strips 42 engage corresponding Velcro strips on the upper surface of the base 32. The Velcro attachment of the base 32 to the cover 34 allows an attendant to gain access to the child at specific locations so as to administer health care. This is illustrated in FIG. 6 opening 43 through which access to the child is provided for equipment 45. While the cover 34 and the base 32 are shown as one continuous portion having a crease 44, it should be understood that they could in effect comprise two portions which are attached along the bottom edge by a similar adhesive material.

Figure 7:
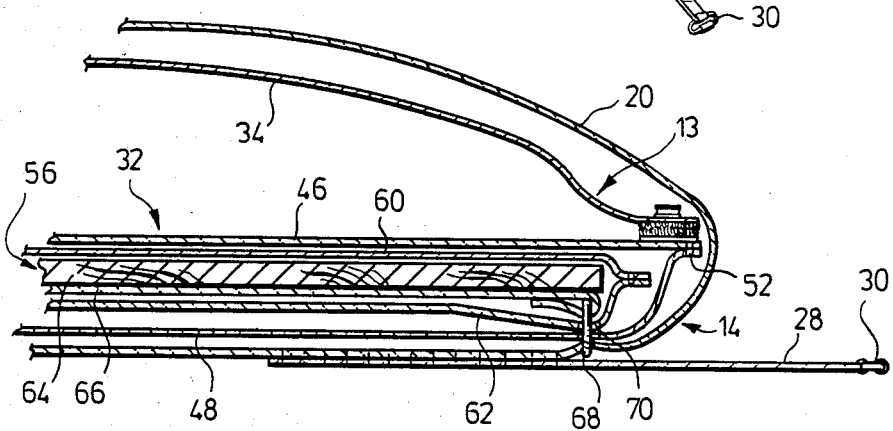
FIG. 7 is a partial side sectional view of the lower end of the apparatus.
Figure 9:
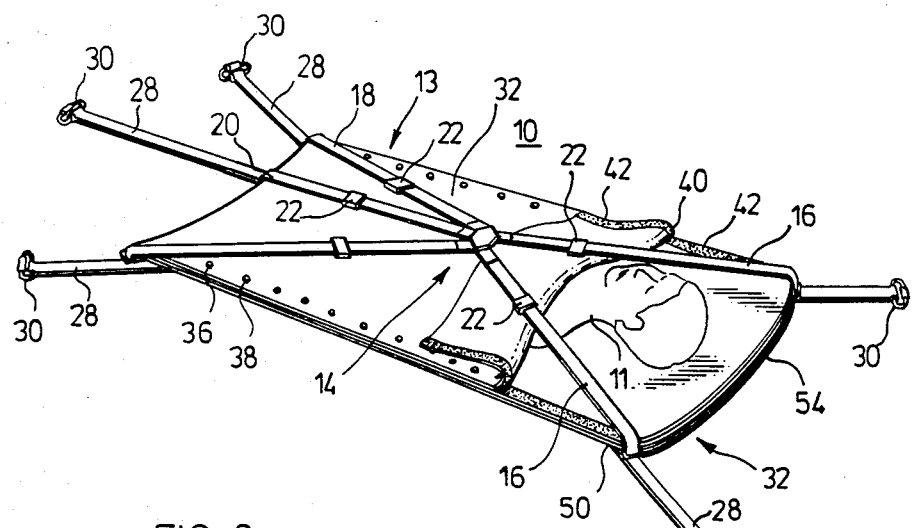
FIG. 9 is a view similar to FIG. 6 showing the semi-rigid base curling about the child.

The base 32 comprises an upper layer 46 and a lower layer 48 which are sewn along side edges 50 and lower edge 52. The upper edge 54 is not sewn so that an opening or pocket 56 (FIG. 2) is defined between the two layers 46 and 48 of the base 32. Each of these layers preferably includes more than one layer of material as discussed hereinafter. Insertable into the pocket 56 is a semi-rigid support 58. Semi-rigid support 58 comprises two layers 60, 62 having sandwiched therebetween, elongated reinforcing members 64. Also provided therebetween are safety webs or straps 66, similar to those straps on the harness 14. The straps 66 extend from opposing corners of the semi-rigid support 58. An additional strap 67 is provided for attachment to perineal strap 20. At the ends of each of these straps 66, 67, there is provided a fastening member in the form of a bracket 68 which passes through a respective aperture 70 on the lower layer 62 of material. Bracket 68 also passes through an aperture of the lower layer 48 of the bag-like support 13 so that the harness straps may pass through brackets 68 as shown in Fig. 7. By using the straps 66 secured in this fashion, any forces acting on the fastening members 68 are evenly distributed over the entire structural support member 58. A stitch pattern is shown at 72 which joins layers 60 and 62 at their edges and between the reinforcing members 64. The straps 66 are held in place by stitching 72. The reinforcing members are spaced apart equidistantly so as to allow the semi-rigid member to be flexible in one dimension which is at right angles to the longitudinal axis of the apparatus. The reinforcing members maintain the apparatus rigid along its longitudinal dimension. Accordingly, this semi-rigid member can act as a spinal splint or the like. Referring to FIG. 9, the apparatus is shown to be curling about a longitudinal axis for the apparatus to partially surround the child.

Figure 8:
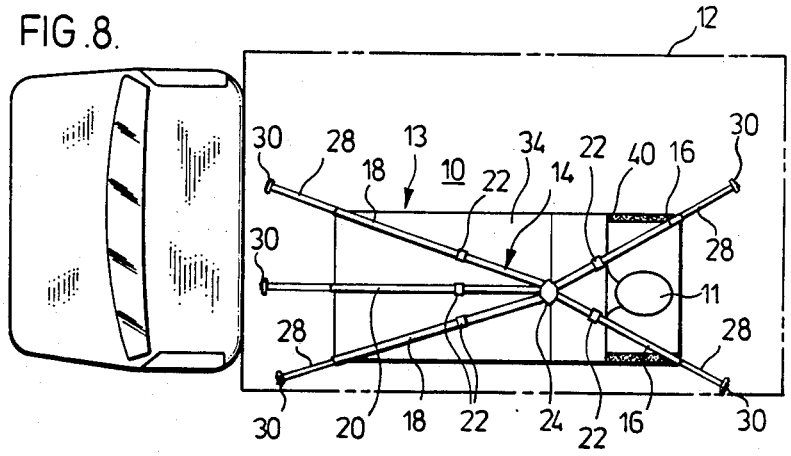
FIG. 8 is a plan view of the apparatus supporting a child within an ambulance.

FIG. 8 illustrates the orientation of the child safety restraining apparatus 10 relative to the ambulance.

Figure 10:
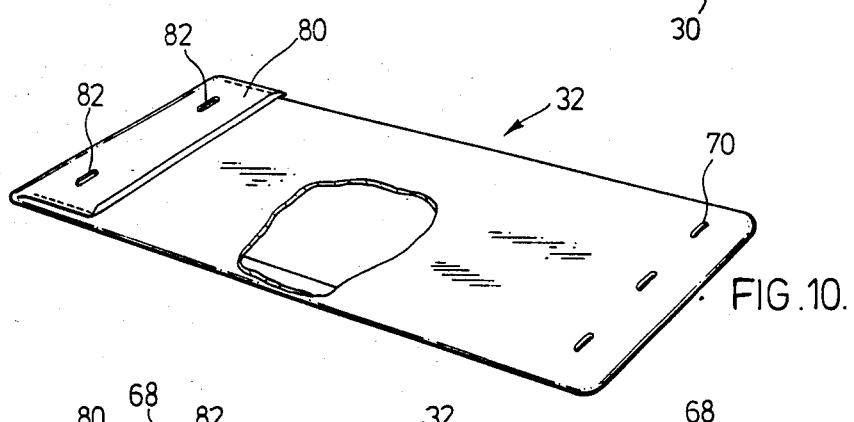
FIG. 10 is a bottom perspective view of the prepared child restraining apparatus showing a fold over flap.
Figure 11:
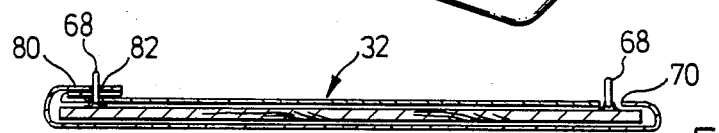
FIG. 11 is a side sectional view of the apparatus of FIG. 10.

Referring to FIGS. 10 and 11 there is shown the bottom view of the base 32 including a flap 80 having apertures 82. Flap 80 extends from the upper layer of material of base 32 over the opening and is secured thereover by fastening members 68 passing therethrough.

Figure 12:
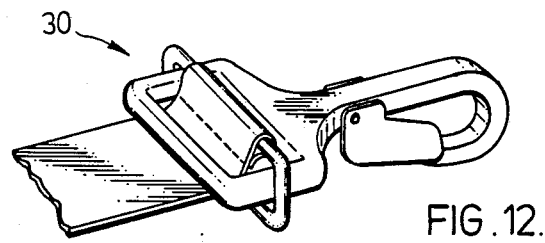
FIG. 12 shows the preferred locking mechanism for the fastening members of the harness.

FIG. 12 shows the preferred form of harness connector 30.

It should be understood that the type of materials used may vary depending on those regulations of the government agencies; however, in the preferred construction, the reinforcing slats or members comprise AA plywood or irradiated polyethylene of an appropriate dimension. The upper layers and lower layers of the child semi-rigid support should comprise a vinyl coated nylon so that this can be sanitized after being soiled. With respect to the cover 34 and the layers 44 and 46 of the base, these may include a suitable cloth material, preferably nylon material which can be removed from the rest of the apparatus and washed. Layers 44 and 46 preferably each include two sheets of nylon material and an intermediate filler layer such as, for example, Dupont Holofill (a trademark). This filler layer provides an insulation and additional bulk over which the harness can be strapped. This filler layer also cushions the child resting above the semi-rigid support or bracing board.

The fastening members 30, 68 are attached to the webbing by sewing the webbing or ends of the strapping members about the fastening members.

The overall dimensions of the child support means are preferably 30 inches long by 20 inches wide. With respect to the harness and any other webbing used, this will be standard safety harness webbing which is presently available in the art.

What is claimed is:

1. A child safety restraining apparatus for restraining a child in a substantially flat position relative to a medical transporting device, comprising:

child support means including a semi-rigid base comprising upper and lower layers of material joined along or adjacent side edges thereof to provide a pocket between the layers of material which is open at one end, the lower layer of material having a plurality of apertures located at predetermined locations therein, a semi-rigid support member insertable into the pocket through the open end, said support member including fastening members secured to the lower surface thereof at predetermined positions which correspond to the location of the apertures in the lower layer of material such that each of the fastening members extends through a corresponding aperture when the support member is inserted in the pocket; said child support means further including a cover attachable to the upper layer of material to protectively secure the child between the upper layer of material of the base and the cover; and restraining means connectable to the fastening members of the child support means to secure the child support means to the transporting device whereby movement of the child support means relative to the transporting device is restrained.

2. The apparatus of claim 1 wherein the cover is foldable to adjust in size and the folded portion is securable to the unfolded portion of the cover.

3. The apparatus of claim 1 wherein the open end of the base includes a flap passing thereover and securable over the opening by the fastening members further extending through apertures in the flap.

4. The apparatus of claim 1 wherein said restraining means comprises a harness that surrounds the child support means to restrain movement of the child.

5. The apparatus of claim 4 wherein said harness includes two shoulder straps, two leg straps and a perineal strap, said straps are adjustable in length, are secured to one another below the child support means, and are securable at one location above the child support means.

6. The apparatus of claim 5 wherein each of said straps includes an attachment strap having a fastening member at its end for securing the harness to the transporting device.

7. The apparatus of claim 1 wherein said cover is detachably attached to the upper layer of material of the base to permit access to the child for administration of health care equipment.

8. The apparatus of claim 7 wherein strips of adhesive material extend along inner surfaces of and adjacent to the periphery of each of the cover and the upper layer of material of the base, the adhesive material of the cover engaging the adhesive material of the base to detachably attach the cover to the base.

9. The apparatus of claim 7 wherein the cover means includes a series of male and female fasteners spaced along the side edges of the upper surface of the cover means, the fasteners allow the cover to be folded and secured along the fold so as to adjust the size of the cover that lies over the child.

10. The apparatus of claim 1 wherein the semi-rigid support member includes a series of elongate reinforcing members spaced apart from each other and secured between two layers of material to make the support rigid in one direction and flexible in a second direction orthogonal to said one direction such the base is bendable about the child.

11. The apparatus of claim 10 wherein the semi-rigid support member includes support webbing extending between the two layers of material from corners of the support member and one intermediate point which cross over each other, the ends of the support webbing adjacent the corners and edge of the support being secured to said fastening member.

12. A child safety support apparatus adapted for connection to a harness secured to a medical transporting device; the child support apparatus comprising a semi-rigid base comprising upper and lower layers of material joined along or adjacent side edges thereof to provide a pocket between the layers of material which is open at one end, the lower layer of material having a plurality of apertures located at predetermined locations therein, said base comprising a semi-rigid support member insertable into the pocket through the open end, said support member including fastening members secured to the lower surface thereof at predetermined positions which correspond to the locations of the apertures in the lower layer of material such that each of the fastening members extends through a corresponding aperture when the support member is inserted in the pocket; said child support means further including a cover attachable to the upper layer of material to protectively secure the child between the upper layer of material of the base and the cover, said semi-rigid support member including a series of elongate reinforcing members equidistantly spaced apart from each other and secured between two layers of material which make the support rigid in one direction and flexible in a second direction orthogonal to said one direction such that said base means is bendable about the child, said semi-rigid support member further including support webbing extending between the two layers of material from corners of the support member and one intermediate point which cross over each other, the ends of the support webbing adjacent the corners and edge of the support member being secured to the fastening members.

* * * * *

UNITED STATES PATENT AND TRADEMARK OFFICE
CERTIFICATE OF CORRECTION

PATENT NO.  : 4,627,428

DATED       : December 9, 1986

INVENTOR(S) : David A. Brooks

It is certified that error appears in the above-identified patent and that said Letters Patent is hereby corrected as shown below:

Column 1, line 13,  "varies" should read --various-- line 14,  "increasing" should read --increasingly--

Column 2, line 3,   "onehalf" should read --one-half-- line 11,  "transportating" should read --transportation-- line 13,  "semirigid" should read --semi-rigid-- line 52,  "semirigid" should read --semi-rigid-- line 62,  "phone" should read --prone--

Column 3, line 40,  "facilitiate" should read --facilitate--

Column 4, line 56,  "transportating" should read --transporting--

Column 7, line 35,  "such the" should read --such that the--

Column 8, line 14,  "therein, said base comprising a" should read --therein, a--

Signed and Sealed this

Seventeenth Day of May, 1988

Attest:

DONALD J. QUIGG

*Attesting Officer*      *Commissioner of Patents and Trademarks*